(12) United States Patent
Tanaami

(10) Patent No.: US 8,264,680 B2
(45) Date of Patent: Sep. 11, 2012

(54) BIOCHIP READER AND ELECTROPHORESIS SYSTEM

(75) Inventor: Takeo Tanaami, Musashino (JP)

(73) Assignee: Yokogawa Electric Corporation, Musashino-shi (JP)

( * ) Notice: Subject to any disclaimer, the term of this patent is extended or adjusted under 35 U.S.C. 154(b) by 0 days.

(21) Appl. No.: 12/550,001

(22) Filed: Aug. 28, 2009

(65) Prior Publication Data
US 2010/0033718 A1 Feb. 11, 2010

Related U.S. Application Data

(60) Continuation-in-part of application No. 10/769,017, filed on Jan. 30, 2004, which is a division of application No. 09/562,317, filed on May 1, 2000, now abandoned.

(30) Foreign Application Priority Data

May 28, 1999 (JP) .................................. 11-149399
May 28, 1999 (JP) .................................. 11-149400
Jan. 17, 2000 (JP) ................................. 2000-007724

(51) Int. Cl.
*G01J 3/00* (2006.01)
*G01N 21/64* (2006.01)
*G01N 33/53* (2006.01)
*G01N 21/76* (2006.01)
*F21V 9/16* (2006.01)

(52) U.S. Cl. .................. 356/300; 250/461.2; 250/483.1; 250/458.1; 422/82.05; 422/82.06; 422/82.07; 422/82.08; 359/819; 359/837; 435/7.1; 356/303; 356/305; 356/317; 356/328; 436/164; 436/171; 436/172

(58) Field of Classification Search ........................ None
See application file for complete search history.

(56) References Cited

U.S. PATENT DOCUMENTS

| | | | |
|---|---|---|---|
| 5,422,712 A | 6/1995 | Ogino | |
| 6,492,125 B2 | 12/2002 | Kauvar et al. | |
| 6,603,537 B1 * | 8/2003 | Dietz et al. | 356/39 |
| 2001/0001581 A1 * | 5/2001 | Tanaami | 359/368 |

(Continued)

FOREIGN PATENT DOCUMENTS

JP 57-207814 A 12/1982

(Continued)

*Primary Examiner* — Neil N Turk
(74) *Attorney, Agent, or Firm* — Westerman, Hattori, Daniels & Adrian, LLP

(57) ABSTRACT

A biochip reader wherein spectroscopic information of a sample under analysis is arranged in spaces between images of the sample arranged on a biochip. The reader comprises a confocal microscope and the biochip comprises a transparent substrate to allow passage of the excitation light and fluorescent light from the sample with the excitation light being applied from the side opposite that on which the samples are arranged so that noise from dust and the like is avoided by the transmitted light avoiding contact with the dust. Another aspect is an electrophoresis system wherein different coloring material are used for each of a variety of target substances, so that the same lane and area are utilizable to concurrently detect a polychrome fluorescent pattern of the different targets. A confocal scanner or fluorescence imaging system is used with a plurality of filters to detect the multi-colored fluorescences of the target substance. Advantageously, in the biochip reader, a lower S/N ration is obtained together with lower cost; and in the electrophoresis system, concurrent detection of multiple polychromatic fluorescence patters is attained.

3 Claims, 18 Drawing Sheets

U.S. PATENT DOCUMENTS

2003/0223059 A1 * 12/2003 Li .................................. 356/317

FOREIGN PATENT DOCUMENTS

| | | |
|---|---|---|
| JP | 58-027029 A | 2/1983 |
| JP | 2-002906 A | 1/1990 |
| JP | 6-043090 A | 2/1994 |
| JP | 8-327452 A | 12/1996 |
| JP | 10-030982 A | 2/1998 |
| JP | 10-206745 A | 8/1998 |
| JP | 11-095109 A | 4/1999 |
| JP | 11-119106 A | 4/1999 |
| JP | 11-133306 A | 5/1999 |
| WO | 98/38510 A2 | 9/1998 |
| WO | 99/23466 A2 | 5/1999 |

* cited by examiner (B)

(A)

(B)

BIOCHIP READER AND ELECTROPHORESIS SYSTEM

RELATED APPLICATIONS

This application is a continuation-in-part of application Ser. No. 10/769,017 which is a divisional application of Ser. No. 09/562,317.

BACKGROUND OF THE INVENTION

1. Field of Invention

This invention relates, in one aspect, to a biochip reader for reading the wavelengths of fluorescence caused by marking samples, e.g. DNA or protein, with a fluorescent substance and then exciting the marked samples; and, in another aspect, to an electrophoresis system used, for example, in bioengineering; and more particularly, to improvements in such biochip reader and electrophoresis system.

2. Description of the Prior Art

The prior art provides a technique wherein DNA (deoxyribonucleic acid) or protein is marked with a fluorescent substance; then the marked substance is excited by irradiation with laser light, and the resulting wavelengths of fluorescence are read so that the DNA or protein is detected and analyzed. In this technique, a biochip is used with samples of DNA or protein is marked with the fluorescent substance being disposed on the surface thereof in spots or arrays.

The biochip is read by irradiating and scanning laser light laterally, for example, to excite spots of the fluorescent substance arranged in arrays. The emitted fluorescent light is then condensed by an optical fiber, for example, and received by an optical detector through an optical fiber to detect the desired wavelength. When reading of one line or array of spots is completed, the biochip is moved longitudinally to repeat the same process. Then, the process is repeated until the biochip is read entirely.

The conventional biochip reader has the following problems:

(1) The biochip is used to process too many spots, has a large outside dimension, and contains thereon too many arrays of spots.

(2) Fluorescence wavelengths are separated by use of an optical fiber. Thus, it is difficult to separate the wavelengths of polychromatic fluorescent light since any spectra mixture thereof depends on the concentration of each color.

(3) The quantity of measurement deteriorates due to the mixing of fluorescent light with self-emission, background light, or the like. This results in decreased accuracy.

(4) A prolonged period of time is required when switching between optical filters and between optical detectors according to the fluorescent color being detected.

(5) The conventional biochip reader can be speeded up by arranging multiple optical filters and optical detectors and causing the various optical detectors to receive fluorescent light at the same time instead of switching between the filters and the optical detectors. However, this approach increases cost for the added equipment.

(6) Using a scanning confocal microscope with the biochip reader increases the number of system components. This results in increased cost and size, and also the time to perform the requirement measurement is increased.

A biochip, such as a DNA chip, used with the reader has a structure in which several thousand to several ten thousand types of known DNA segments are arranged in arrays on a substrate. If any unknown DNA segment is flowed onto the DNA chip, it is combined with a DNA segment of the same type. Taking advantage of this property of DNA, a known DNA segment, that has formed a combination, is examined by the biochip reader to identify the properties of the unknown DNA, such as DNA arrangement.

FIG. 1 shows an example of hydridizing a biochip, wherein six types of DNA segments DN01-DN06 are arranged in arrays on a substrate SB01 to form a DNA chip. UN01 is an unknown DNA segment and was previously provided a fluorescent mark, as indicated by LM01. When hybridized to the DNA chip, the unknown DNA segment UN01 combines with another DNA segment whose arrangement is complementary. For example, the unknown DNA segment UN01 combines with known DNA segment DN01, as indicated by CB01. Using a biochip reader, excitation light is irradiated at the DNA chip, thus hybridized, in order to detect fluorescent light emitted from the fluorescent mark. Thus, it is possible to determine which of the known DNA segments the unknown DNA segment combined with. For example, in an image resulting from scanning the DNA chip, indicated by SI01, fluorescent light is observed only at a spot where the DNA combination CB01 has been produced. This means fluorescent light is detected only from spot CD01.

FIG. 2 shows an example of a conventional biochip reader, wherein a light source 1 (e.g. a laser) emits excitation light, to a dichroic mirror 2 which reflects light to an objective lens 3 which focuses the light onto a DNA chip 4 which is a biochip onto which a plurality of cells are arranged in an array. The reflected light is transmitted to a filter 5, lens 6 and then to optical detector 7, such as a photo multiplier tube.

The cells CL01-CL03 in which DNA segments, namely, samples, of the same type are arranged on biochip 4.

Light emitted from the light source 1 is reflected by the dichroic mirror 2 as excitation light and condensed onto cells on the DNA chip 4 through the objective lens 3. For example, the excitation light is condensed onto the cell CL02. Fluorescent light produced by the excitation light in cell CL02 becomes parallel light after passing through objective lens 3 and then passes through dichroic mirror 2. Fluorescent light that passed through dichroic mirror 2 then travels through filter 5 and is condensed onto the optical detector 7 by lens 6.

The DNA chip 4 is scanned by a drive means, not shown. For example, the DNA chip 4 is scanned in the direction indicated by arrow MV01 so that the excitation light is irradiated at cells CL01-CL03 on chip 4. Hence, it is possible to identify the arrangement of the unknown DNA segment from the position of a cell where the fluorescence has taken place. That is, fluorescence takes place where the DNA segment to be identified combines with a complementary DNA segment and that combination will be excited to fluoresce.

Unfortunately in most environments, dust may deposit on the DNA chip 4 when mixing foreign matter with a liquid in which the unknown DNA segment is hybridized or when subsequent processes are carried out. If the dust is organic, the excitation light may cause the dust to emit fluorescent light that is more intense than that emitted by a cell. This results in unwanted noise, and deteriorates the S/N ratio.

FIG. 3 is an enlarged view of the cell CL02 of FIG. 2, wherein objective lens 3 and biochip 4 are shown with cell CL02 disposed on the biochip 4. If the DNA chip 4 is contaminated with dust particles, e.g. marked DS01 and DS02, fluorescent light LL11 is produced by the excitation light in addition to fluorescent light emitted from cell CL02. This will cause deterioration of the signal to noise ratio (S/N). For this reason, a confocal optical system has been used as a conventional biochip reader to detect only the fluorescent light produced by the cells by removing fluorescent light produced by the dust. Alternatively, another solution to the dust problem is to hermetically seal the chip 4 and prevent it from being contaminated with dust. However, these measures are not satisfactory because of the problems caused thereby, such as increased cost and insufficiently improved S/N.

In addition, an electrophoresis method has been used to analyze the structure of genes and proteins, such as amino acid, because such method is inexpensive and simple. The methods are often used in the field of bioengineering. The different electrophoresis methods include a disk electrophoresis method using polyacrylamide, an SDS (sodium dedecyl sulfate) polyacrylamide-gel electrophoresis method, an isoelectric point electrophoresis method, a nucleic acid gel electrophoresis method, an electrophoresis method based on the effects of interaction with other molecules, a two dimensional electrophoresis method, and a capillary electrophoresis method.

FIG. 4 shows an exemplary conventional electrophoresis measurement system comprising an electrophoresis unit 10 and a signal processor 20. The electrophoresis unit 10 consists of a lane area 11, a first electrode 12 and a second electrode 13 for applying voltage to the lane area 11, a support plate 14 for supporting the lane area 11 and the first electrode 12 and second electrode 13, a power unit 15 for electrophoresis used to supply voltage to the two electrodes 12 and 13, a light source 16 for emitting light to excite a fluorescent substance, an optical fiber 17 for guiding light emitted by the light source 16, and an optical detector 18 for condensing fluorescent light produced by a fluorescent substance to convert the light to an electric signal after selectively introducing light of a specific wavelength through an optical filter.

The signal processor 20 receives an electric signal from the optical detector 18 to perform appropriate processes, such as converting the electrical signal to digital data or performing preliminary processes, including summing and averaging. The output signal from the processor 20 is supplied to a data processor (not shown) where samples are examined and analyzed.

In the FIG. 4 system, electrophoresis begins when a gel is injected into the lane area 11, samples of DNA segments marked with a fluorescent substance are injected from the gel, and voltage is applied to the first electrode 12 and the second electrode 13 using power unit 15. Molecules contained in the samples gather in each lane of samples as classified by molecular weight, each group of molecules forming a band. Since molecules having lower molecular weight have higher speeds of electrophoresis, they migrate longer distances within the same period of time. These bands are detected by irradiating the gel with laser light, for example, emitted by light source 16, causing marks of the fluorescent substance that concentrate on the bands in the gel to emit fluorescent light, and detecting the fluorescent light with the optical detector 18.

When the gel is irradiated with laser light, the fluorescent substance within part of the gel, which exists along a line L1 shown in FIG. 5, is excited to emit fluorescent light. The fluorescent light is detected at a given position in each lane, as it is searched for in the direction of electrophoresis with the lapse of time. Hence, the fluorescent light is detected when a band B2 of each lane crosses line L1. Thus, it is possible to a signal representing the intensity pattern of fluorescence of a single lane. The data processor which is not shown is designed to analyze each base sequence of the DNA from the pattern signal.

The conventional electrophoresis system has the following problems:

(1) A prolonged time period is required to perform measurement.

(2) The separability of cells is not sufficient. Too many lanes are required in order to separate a variety of DNA segments. Also, information on the correlation among three or more dimensions is not available since the system is limited to two dimensional analysis.

(3) The system requires a large installation space, such as, for example, a lane area as large as 50 cm×50 cm or 5 cm×5 cm.

(4) A two dimensional system is particularly inferior in terms of positional reproducibility. This problem may be solved by applying markers to other lanes and then referencing the added markers. However, applying added markers, disadvantageously, increases lane area needed for analysis.

SUMMARY OF THE INVENTION

Accordingly, an object of the invention is to overcome the aforementioned and other problems, disadvantages, and deficiencies of the prior art.

Another object is to provide a biochip reader which can simultaneously achieve three objectives: downsizing, cost reduction, and improvement of accuracy.

A further object is to provide a biochip reader having an improved S/N ratio, and whose cost is reduced.

A still further object is to provide an electrophoresis system which has a compact lane area, offers highly accurate electrophoresis patterns, and enables rapid acquisition of large amounts of interrelated information.

The foregoing and other objects are attained by the invention which encompasses in one aspect a biochip reader wherein light is irradiated at a biochip onto which a plurality of samples are arranged in spots or linear arrays and image date of the plurality of samples is read out using an optical detector. The biochip reader comprises means for arranging multiple pieces of spectroscopic information of the samples under analysis in spaces between the images of the samples. According to the biochip reader, it is possible to output pieces of spectroscopic information of the samples into spaces between the images of the samples and thereby realize easy, simple and concurrent multiwavelength measurement. According to the invention, it is also possible to acquire multi-wavelength information using a compact biochip reader.

The invention further encompasses a biochip reader which comprises a light source for emitting excitation light, a dichroic mirror for reflecting or transmitting the excitation light, an objective lens for condensing the excitation light reflected or transmitted by the dichroic mirror and projecting fluorescent light produced at the biochip onto the dichroic mirror, an optical detector for detecting the fluorescent light, and a lens for condensing the excitation light reflected or transmitted by the dichroic mirror onto the detector. In this arrangement, the biochip is fabricated using a transparent substrate that can transmit both the excitation and fluorescent light with the excitation light being irradiated from the side opposite to the side where the samples are arranged on the biochip. Advantageously, the invention has improved S/N ratio and reduces the cost.

Another aspect of the invention encompasses an electrophoresis system wherein a sample marked with fluorescent coloring matter is caused to migrate in a lane area and the pattern of fluorescence thereof is read out. The system comprises an electrophoresis unit for flowing a plurality of samples, which are prepared by combining a different type of fluorescent coloring matter with each of a variety of target substances, such as protein or DNA, through the same lane in the lane area, and a confocal scanner or a fluorescence imaging system which scans the samples in the lane area with excitation light and the polychrome fluorescence patterns of the samples that emit fluorescent light when irradiated with excitation light are detected concurrently through multiple filters with different transmission characteristics. Advantageously, the number of lanes is reduced, and hence, the size of the lane area is reduced. Moreover, the voltage gradient and gel are prevented from becoming uneven. Thus, advantageously, precision measurement is performed with the invention. Moreover, simultaneous detection is provided of the polychrome fluorescence patterns using the confocal scanner or fluorescence imaging system, thus reducing the time required for detection.

DETAILED DESCRIPTION OF THE PREFERRED EMBODIMENTS

Figure 6:
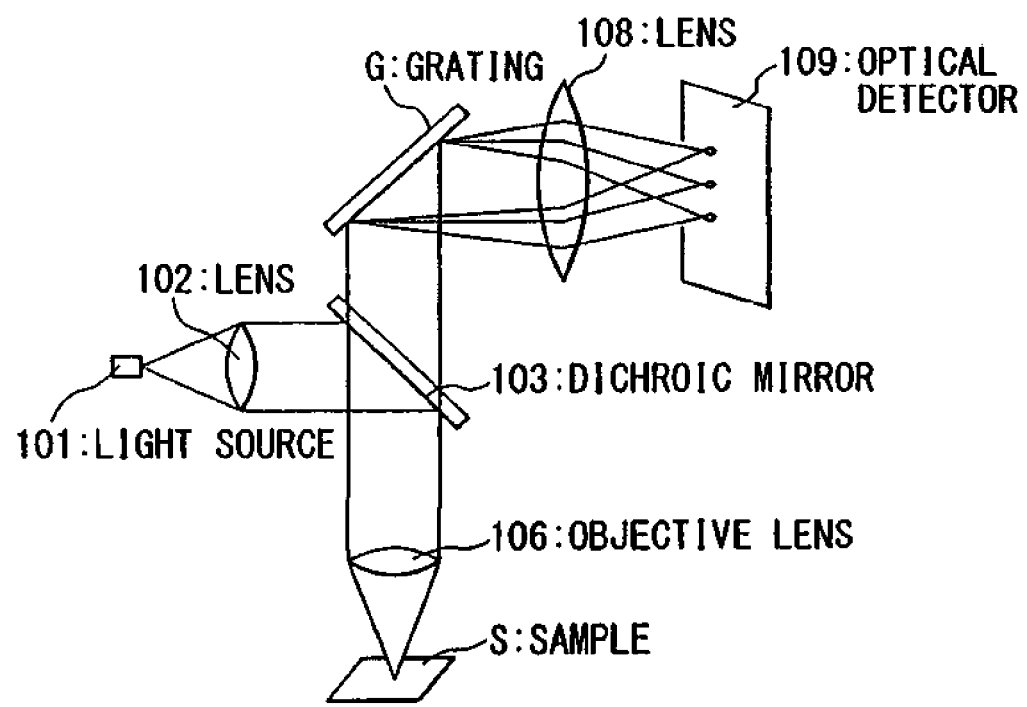
FIG. 6 is a block diagram depicting an illustrative biochip reader of the invention.

In FIG. 6, the biochip reader comprises a light source 101 for emitting laser light (or other types of excitation light), a lens 102 for causing the light to be parallel, a dichroic mirror 103, an objective lens 106, a sample S, a grating G, a lens 108, and an optical detector 109. The excitation light emitted by light source 101 is made to travel in parallel beams by lens 102, reflected by dichroic mirror 103, condensed through objective lens 106 and irradiated onto sample S. The irradiation causes sample S to emit fluorescent light, whose wavelength differs from that of the excitation light. The fluorescent light then traces the path followed by the excitation light and passes through objective lens 106 and reaches dichroic mirror 103, and then is diffracted by grating G. The diffraction angle of the fluorescent light is relative to its wavelength. The fluorescent light thus diffracted by grating G is condensed onto optical detector 109 through lens 108. The optical detector 109 may comprise, for example, a camera.

Figure 7:
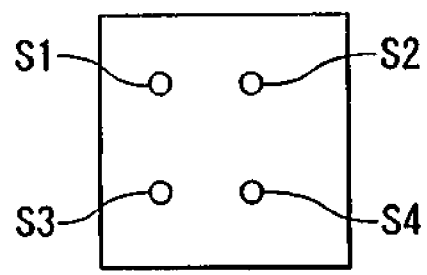
FIG. 7 is a schematic view depicting an arrangement of samples on a biochip.
Figure 8:
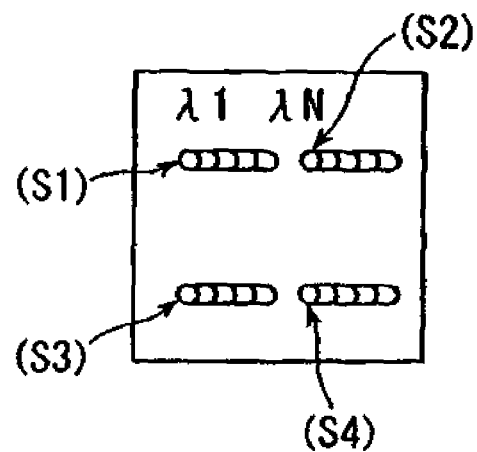
FIG. 8 is a schematic view depicting pieces of spectroscopic information indicated on an optical detector.

If, for example, spots of four samples S1-S4 are arranged on a biochip, such as shown in FIG. 7, spectroscopic images, or spectra, with wavelengths of $\lambda 1$-$\lambda n$ are formed for the respective samples in spatially different positions on the optical detector 109, as shown in FIG. 8. The spectroscopic images are spectroscopic information and can be measured with a monochrome camera. As can be seen from the drawing, gaps between the spots are used in the invention.

Figure 9:
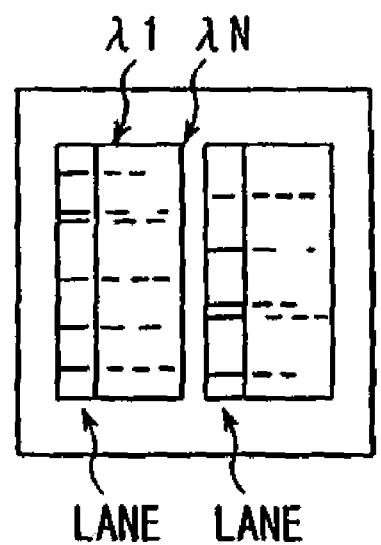
FIG. 9 is a schematic view depicting pieces of spectroscopic information provided when samples, arranged in linear arrays, are measured.

Although the embodiment is based on use of a biochip on which spots are disposed in arrays, the invention is not so limited. Fluorescence patterns of electrophoresis arranged in linear arrays may also be used. In this case, for example, images shown in FIG. 9 are obtained. That is, spectroscopic images with wavelengths of $\lambda 1$-$\lambda n$ are formed for the electrophoresis pattern of each lane (e.g. along the longitudinal axis) in spatially different positions along the lateral axis.

Figure 10:
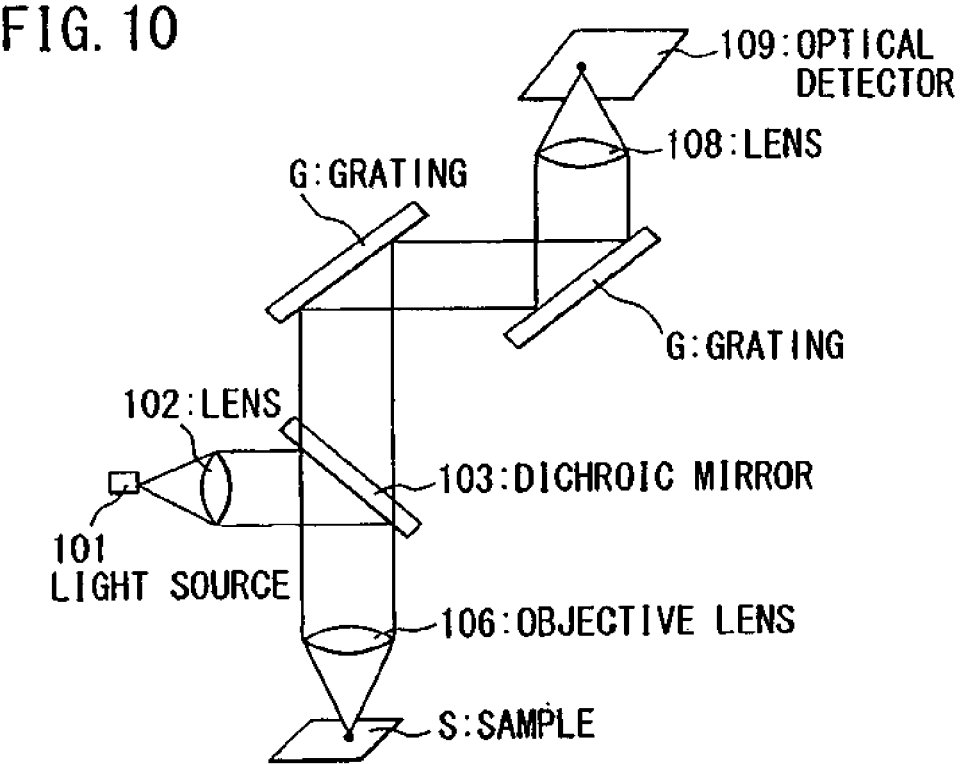
FIG. 10 is a block diagram depict another illustrative embodiment of the invention.
Figure 11:
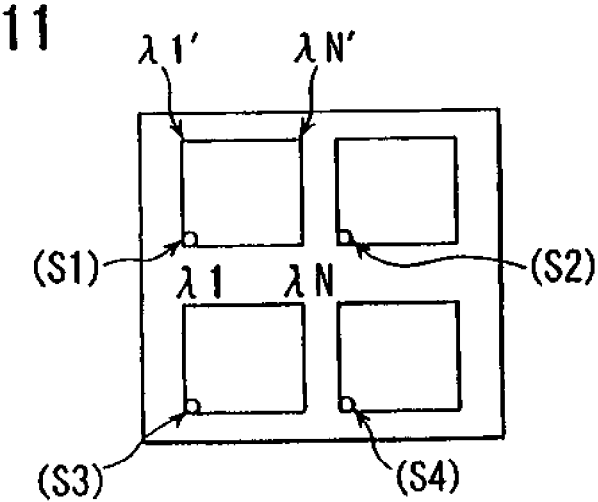
FIG. 11 is a schematic view depicting spectroscopic images obtained when pieces of spectroscopic information are developed in two dimension.

FIG. 10 shows another embodiment, wherein two gratings are arranged so that their directions of diffraction are at right angles to each other. According to the embodiment, two dimensional spectra are obtained as shown in FIG. 11. If, for example, the spectral pattern is graduated in 100 nm increments laterally (e.g. X-axis direction) and in 10 nm increments longitudinally (e.g. Y-axis direction), it is possible to perform measurement with a wider dynamic range and higher precision.

Figure 12:
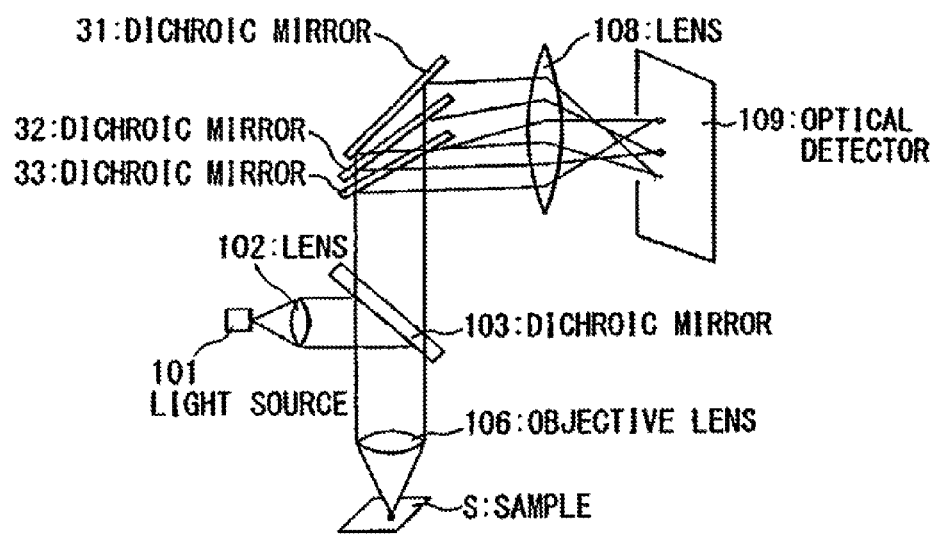
FIG. 12 is a block diagram depicting a further illustrative embodiment of the invention.

FIG. 12 shows an embodiment wherein dichroic mirrors 31-33 are used in place of the gratings G in FIG. 10. These dichroic mirrors 31-33 may be combinations of optical filters with optical shift means. As shown in FIG. 12, dichroic mirrors (e.g. optical filters) 31, 32 and 33 with different transmission wavelengths are stacked on the optical axis. In this embodiment, the angle of each dichroic mirror is determined so that light is reflected by the dichroic mirror at the same angle as it would have been diffracted with a grating (i.e., equivalent to the optical shift means).

Figure 13:
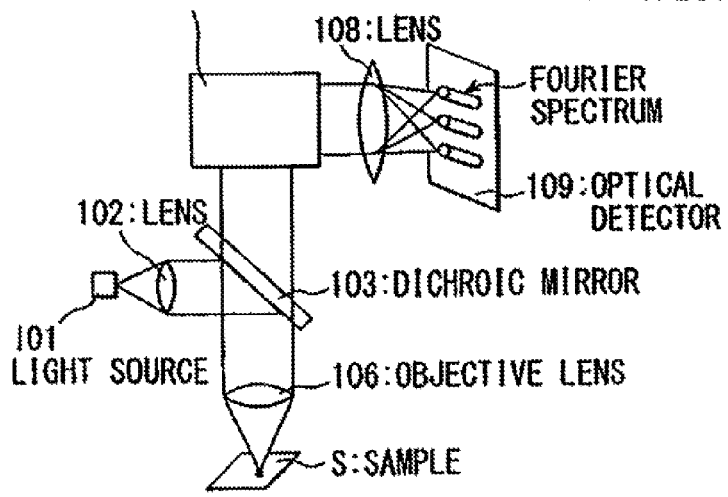
FIG. 13 is a block diagram depicting a further illustrative embodiment of the invention.
Figure 29:
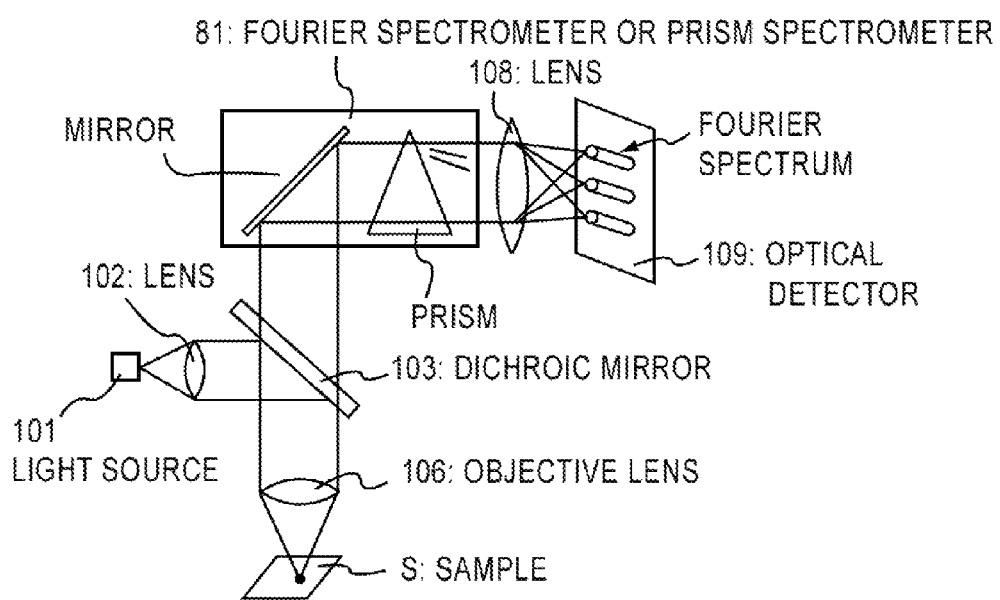
FIG. 29 is a block diagram depicting a further illustrative embodiment of the invention including a prism spectrometer.

FIG. 13 is an embodiment wherein non-moving Fourier spectrometer 81, such as a Savart or a Michelson model, is used in place of the gratings (G of FIG. 10), or dichroic mirrors (31-33) of FIG. 12. In, this embodiment, images formed at the optical detector 109 are not spectra per se but are images of interference fringes. Hence, spectra can be obtained by using computation means (not shown) and submitting the image to a Fourier transform process. Further, a prism spectrometer may be used as a refractive spectroscopic means (illustrated in FIG. 29).

It should be noted that the measurement resolution can be further improved using a confocal microscope or a 2 photon microscope instead of a regular fluorescent substance or a camera. The quantity of measurement is also improved because the slice effect of the confocal method allows measurement of a constant volume of samples always even when the thickness of each sample is varied. Meanwhile, in this case (in the embodiment of FIG. 13), the confocal microscope may be of the non-scanning type. If the Raman microscope of Raman spectroscopy is combined with the optical system described above, spectroscopic characteristics of the samples can be measured even if the samples are not stained. Spectroscopic spectrum allows spectroscopic image to be arranged in free spaces between the images of the sample in the same manner as shown in FIG. 8, FIG. 9 and FIG. 11.

Figure 28:
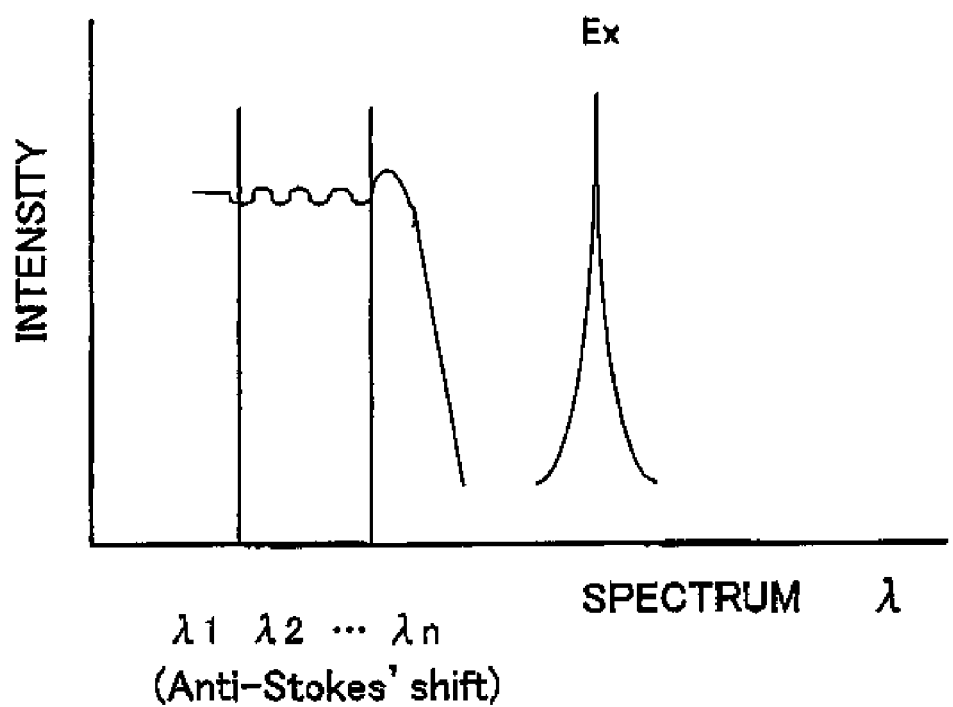
FIG. 28 is a schematic view depicting the vibration information of molecules becomes spectroscopic spectrum.

If the substance is irradiated with an excitation light Ex of a certain wavelength, light having the same wavelength is scattered (Rayleigh scattering), but a part of the scattered light is varied in wavelength depending on vibration of the wavelength of the scattered light of the Raman scattering being lengthened is defined as a stokes scattering, and the wavelength of the scattered light thereof being shortened is defined as an anti-stokes scattering. As shown in FIG. 28, vibration information of molecules becomes spectroscopic spectrum.

Figure 14:
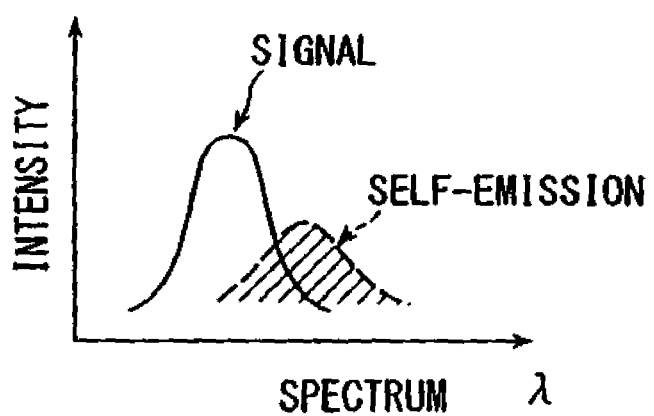
FIG. 14 is a graph depicting distribution of self-emission.

As shown in FIG. 14, noise, such as from self-emission, whose wavelength differs slightly from that of the original fluorescent light can be removed easily because the properties of the reagent being used are known. If necessary, a signal spectrum may be separated using a regression method. With this approach, it is possible to achieve high precision and high sensitivity with the invention.

For spectroscopy, it is necessary to restrict the area of measurement using a shield means, such as slits. If the area of the shield means is greater than the area of the sample, dead spaces are produced in the imaging area of an optical detector. Conversely, if the area of the shield means is smaller than the area of the sample, dead spaces are produced in the area of the sample.

Figure 15:
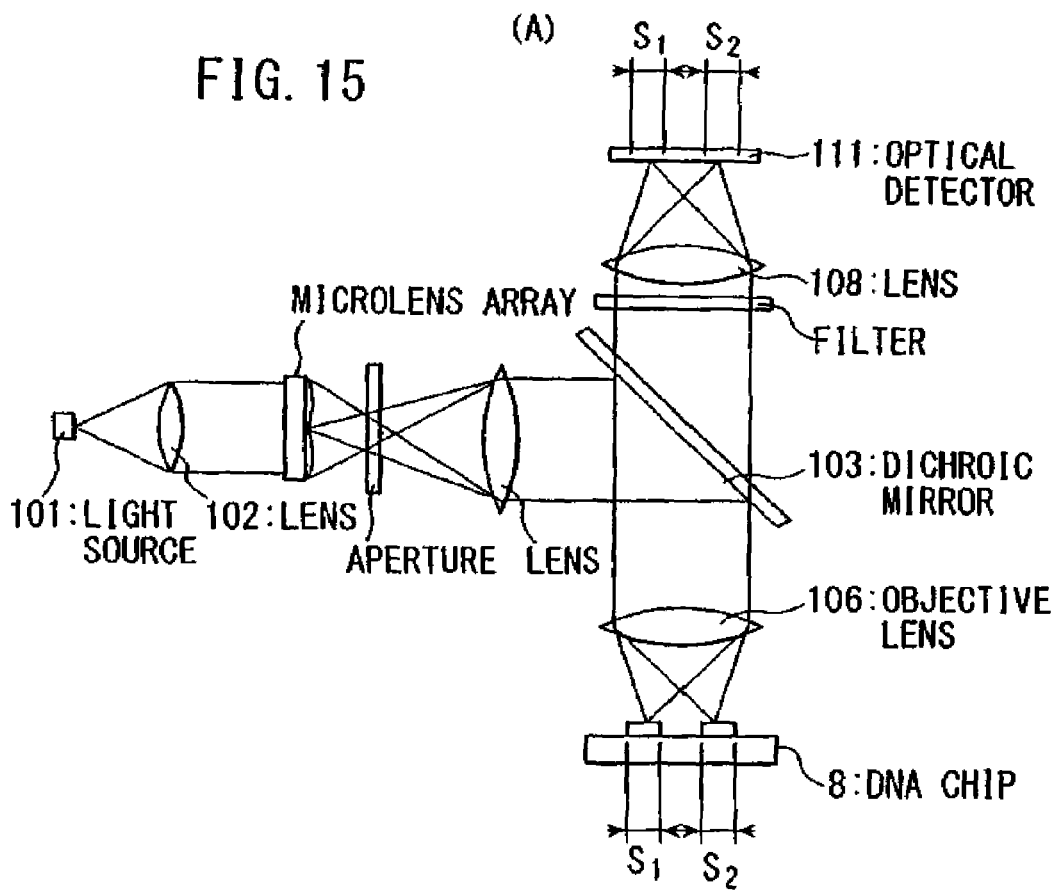
FIGS. 15(A) and 15(B) are schematic views depicting relationship between samples and apertures.
Figure 15:
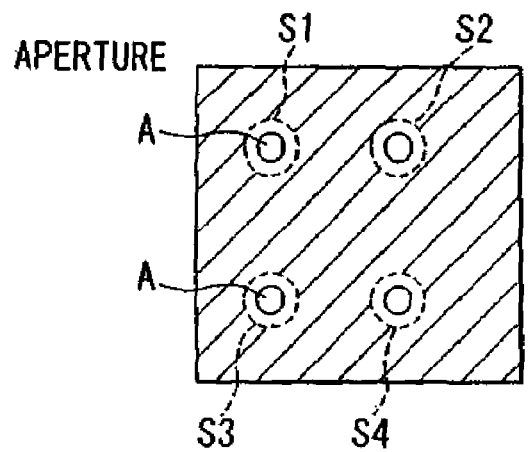

For these reasons, as shown in FIGS. 15(A) and (B), an aperture A may be optically aligned with the area of sample S1 or with part of sample S1, for example. This arrangement provides effective use of both the area of sample S1 and imaging area of the optical detector. This arrangement also eliminates errors due to non-uniformity in the edges of a sample. The shape of the aperture need not be circular; a rectangular shape is acceptable, for example. The aperture may be used as a pin hole or slit for a non-scanning confocal microscope. With this approach, it is possible for even a small and inexpensive microscope to achieve high resolution and other properties of a confocal microscope and quantativeness due to the slice effect.

In the embodiment of FIGS. 15(A) and (B), the detection means is not limited to use of a spectroscopy method, as shown in FIG. 6, but may also be a regular filter method. Luminous energy can be increased further by attaching a microlens array to the light source side of an aperture. Use of the microlens array eliminates the need for the aperture since light beams are condensed onto the focal point of each microlens.

The invention attains the following and other advantages.

(1) Multiple wavelengths of fluorescence can be measured concurrently without having to change the filter and/or optical detector. A compact biochip reader is realized with the invention.

(2) A monochrome camera may be used to photograph spectra displayed on an optical detector; hence, economical analysis is provided.

(3) Spectra displayed on an optical detector can be easily changed to two dimensional spectra; hence, higher precision is attained.

(4) The given area of a biochip can be most effectively used by aligning the aperture of excitation light or spot of light condense microlens array with a sample to be analyzed.

Figure 1:
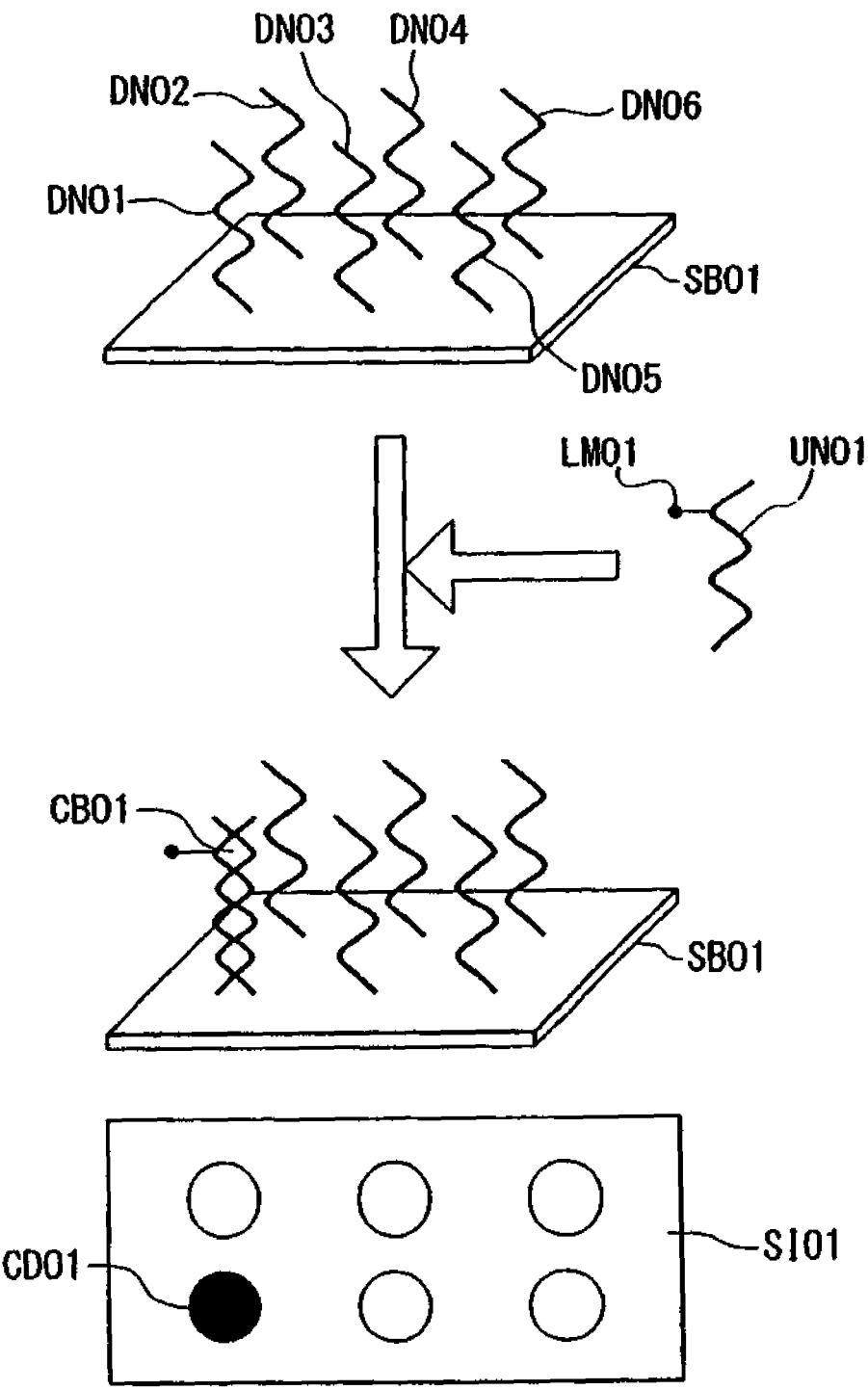
FIG. 1 is a schematic view depicting a conventional hybridization in biochips.
Figure 2:
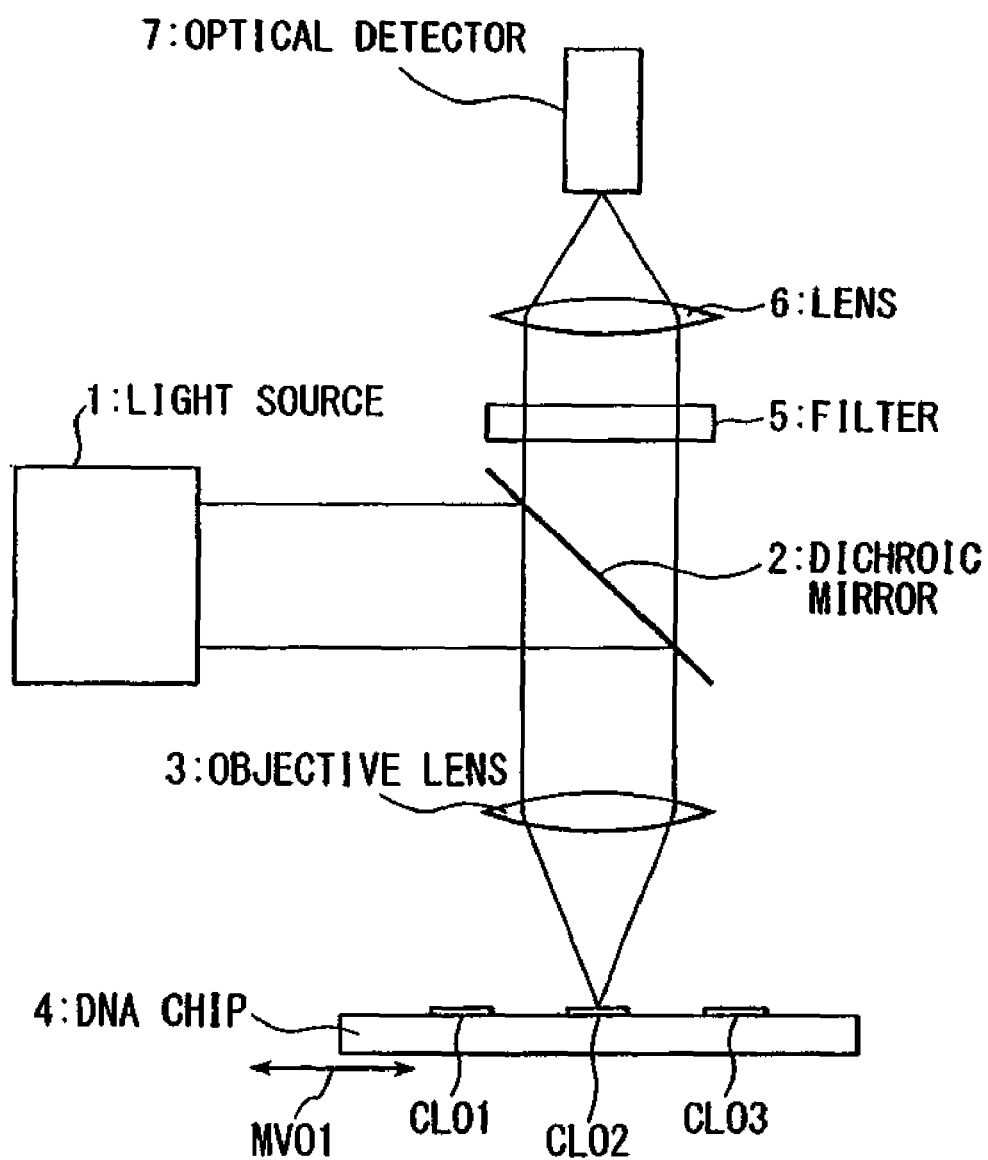
FIG. 2 is a block diagram depicting a conventional biochip reader.
Figure 3:
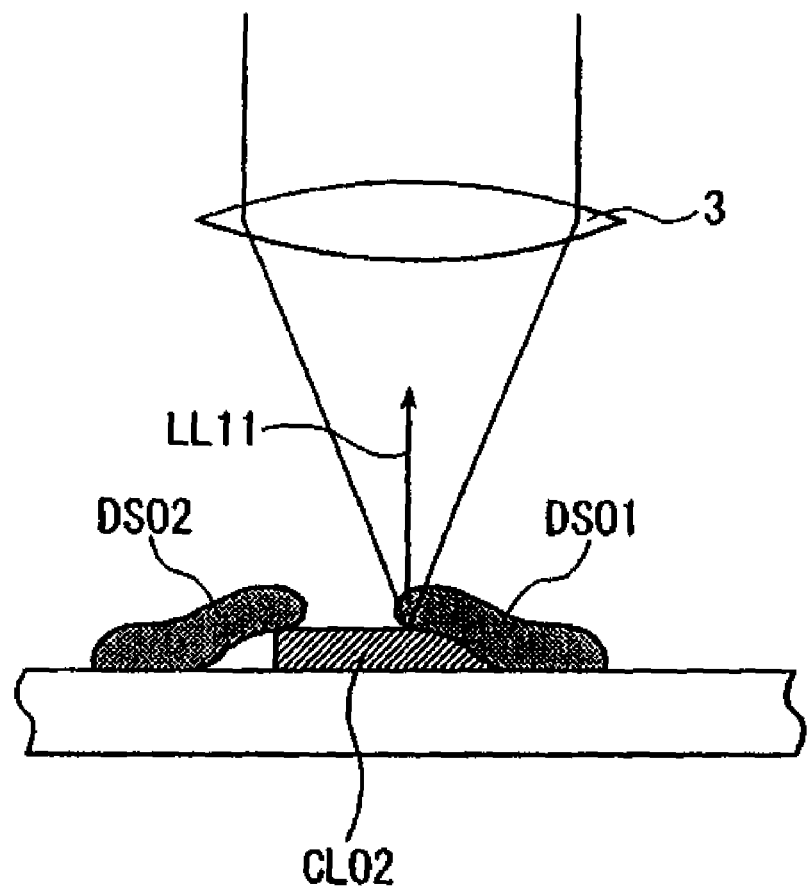
FIG. 3 is an enlarged view of the cell of FIG. 2.
Figure 4:
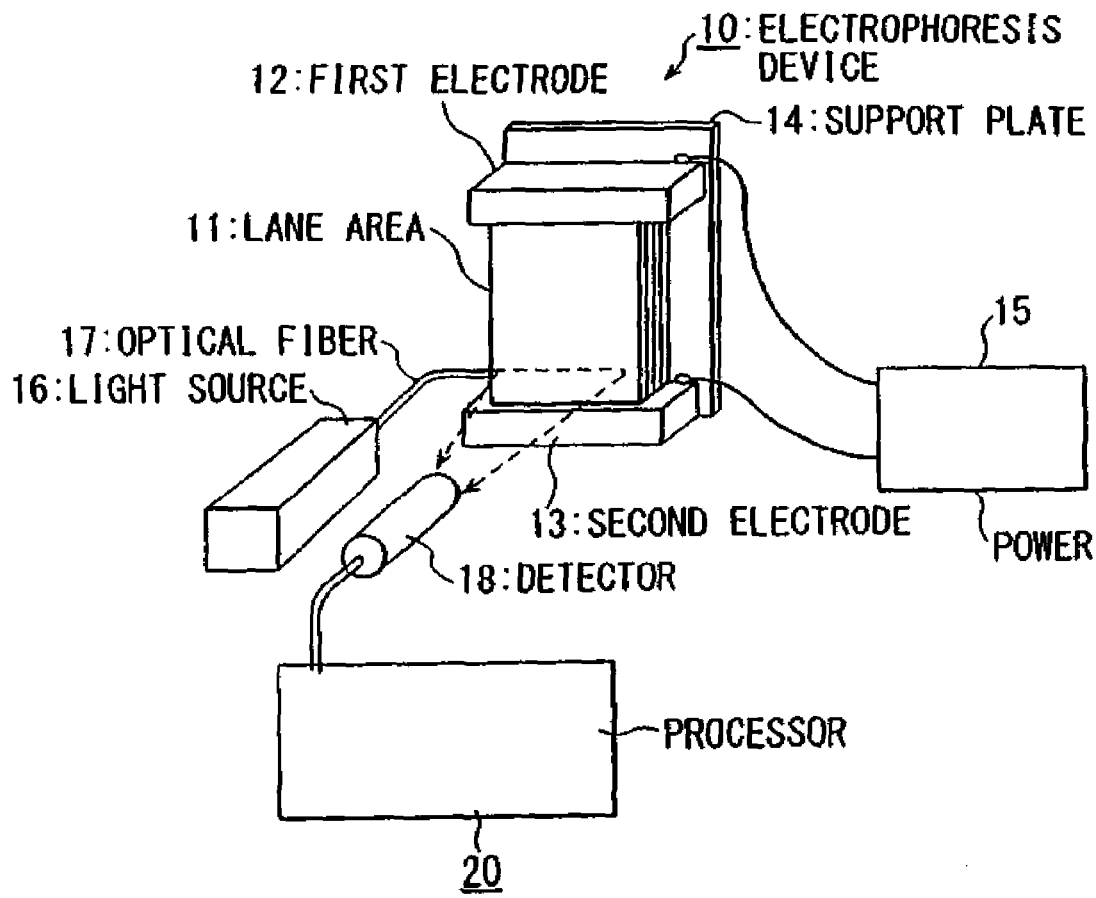
FIG. 4 is a schematic view depicting a conventional electrophoresis system.
Figure 5:
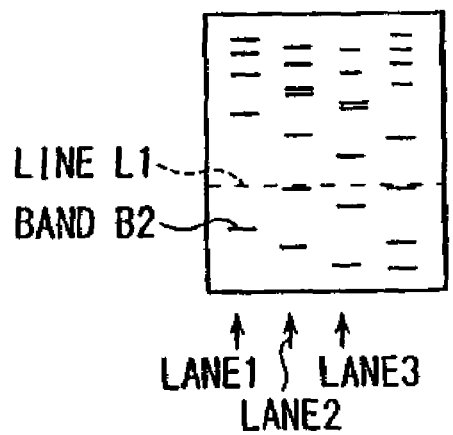
FIG. 5 is a prior art pattern of electrophoresis.
Figure 16:
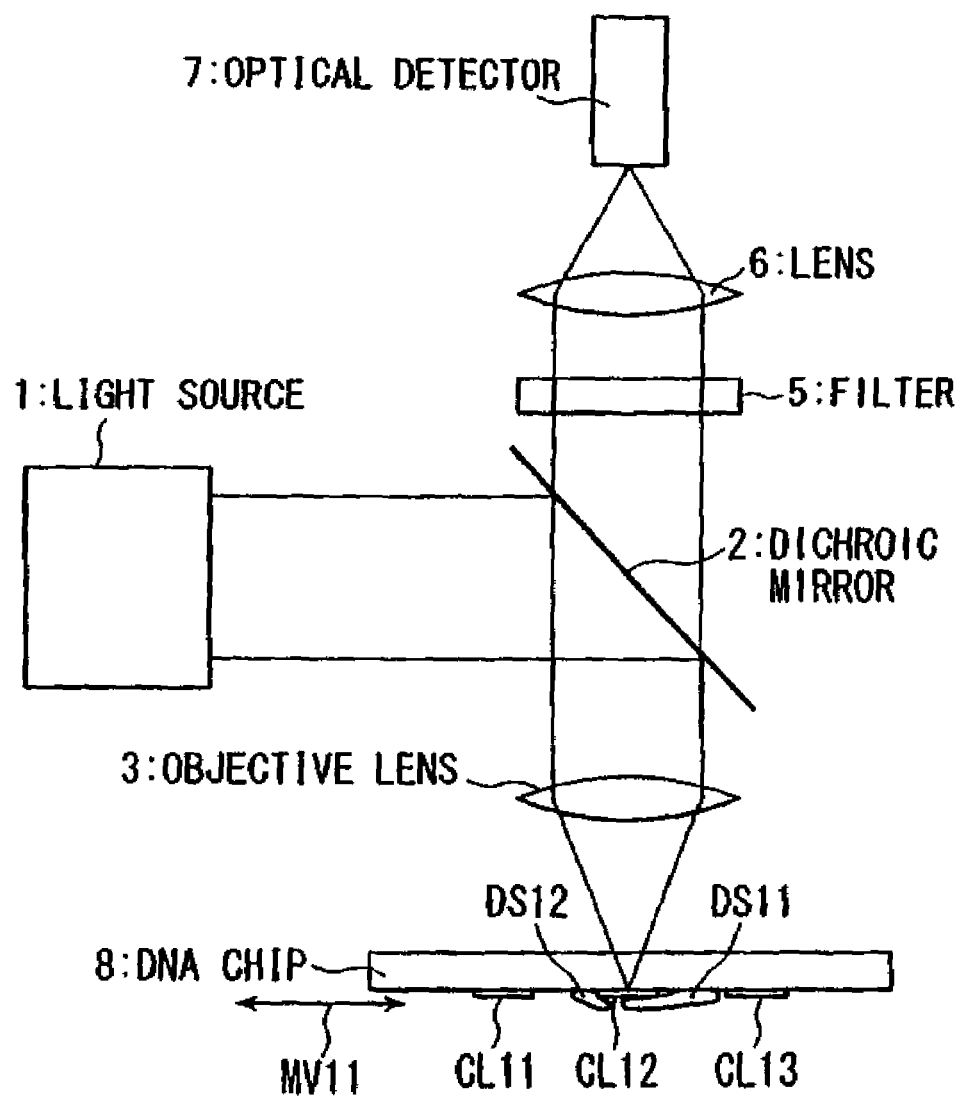
FIG. 16 is a block diagram depicting an illustrative biochip reader of the invention.

FIG. 16 shows a biochip reader, wherein components indicated by numerals 1 to 3 and 5 to 7 are the same as in FIG. 2, and number 8 indicates a DNA chip using a plastic or glass substrate which is transparent and allows excitation light and fluorescent light to be passed there through. Components indicated by symbols CL11 to CL13 are cells, such as those described with reference to samples of DNA segments of the same type being arranged. The symbols DS11 and DS12 indicate dust particles adhering to the cell CL12 on DNA chip 8.

Light emitted as excitation light from light source 1 is reflected by dichroic mirror 2 and condensed onto a cell on DNA chip 8 by objective lens 3. At this point, the excitation light is irradiated from the side opposite to the side where the cells are arranged, as depicted. For example, excitation light is irradiated at the cell CL12 through the transparent substrate of DNA chip 8. Fluorescent light produced by the excitation directed at the cell, is transmitted and made parallel through objective lens 3, and passed through the dichroic mirror 2. The fluorescent light is then condensed by lens 6 onto optical detector 7 through a filter 5. At this point the fluorescent light produced by the excitation light at the cell passes through the DNA chip 8 and is outputted through the side opposite that where the cells are arranged.

The DNA chip 8 is scanned by a drive means which is not shown. For example, the DNA chip 8 is scanned in directions shown by arrows MVI so that the excitation light is irradiated also at cells CL11 and CL13 in addition to cell CL12.

Liquid in which unknown DNA segments are hydridized is flowed onto the side where the cells, such as cell CL12, are arranged. The dust particles DS11 and DS12 adhere to the side of the DNA chip 8 where the cells are arranged.

On the other hand, no foreign matter, such as dust particles DS11 adheres to the side opposite to the side where the cells are arranged on DNA chip 8. Thus, fluorescent light resulting from the dust particles, and being a noise factor, is reduced by irradiating the excitation light from the side of chip 8 opposite to the side whereat the cells are arranged. For example, the excitation light is irradiated at the area of a boundary between the substrate of the DNA chip 8 and a cell.

In addition, advantageously, a simple optical system can be used as the biochip reader without any need for hermetically sealing the chip. Hence, the cost of the biochip reader is reduced. Also, it should be noted that although only a DNA chip is shown as an example of a biochip, the invention is not so limited. The biochip may incorporate, for example, array segments of ribonucleic acid (RNA), protein or sugar chain placed on a transparent chip. With respect to the RNA segments, such RNA segments also undergo hydridization, while the protein and sugar chain segments are submitted to an antigen antibody reaction. In either case, segments of known samples combine with segments of unknown segments marked with a fluorescent substance.

Figure 17:
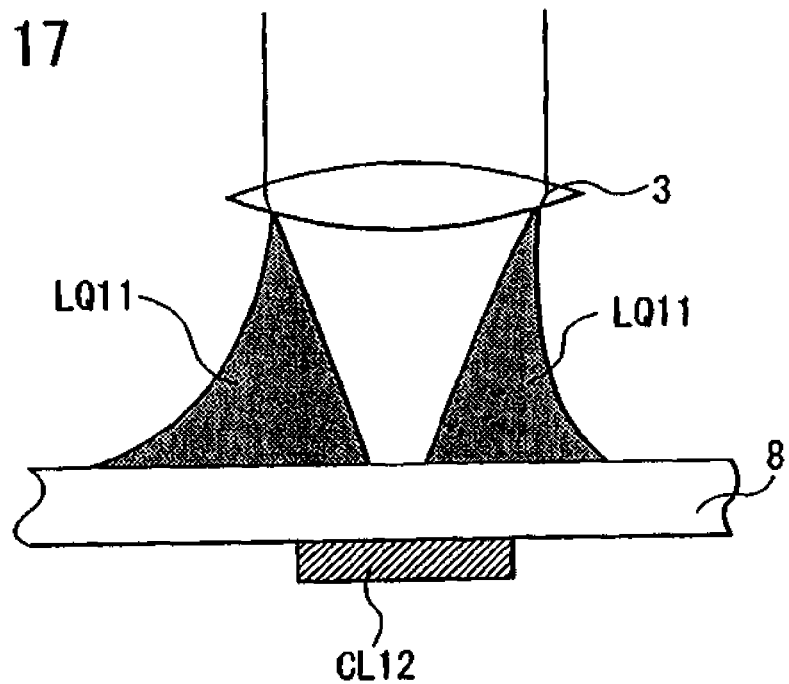
FIG. 17 is a partially enlarged view depicting a cell when an immersion lens is used.

Although the objective lens shown for example in FIG. 16 is of the non-immersion type, the objective lens may also be of the immersion type, such as water immersion or oil immersion lens. FIG. 17 is a partially enlarged view of cell CL12 shown in FIG. 16 with an immersion lens 3 being used. Components labeled 3, 8 and CL12 in FIG. 17 are the same as those in FIG. 16.

In FIG. 17, symbol LQ11 indicates a fluid, such as water or oil, filled into the gap between the objective lens 3 and DNA chip 8. In this arrangement, the numerical aperture (NA) is improved, thereby improving further the signal to noise (S/N) ratio, because of the refractive index of fluid, such as water or oil. For this arrangement, however, the method of scanning is to scan the beams of excitation light per se rather than scanning the DNA chip 8 or the objective lens 3.

Figure 18:
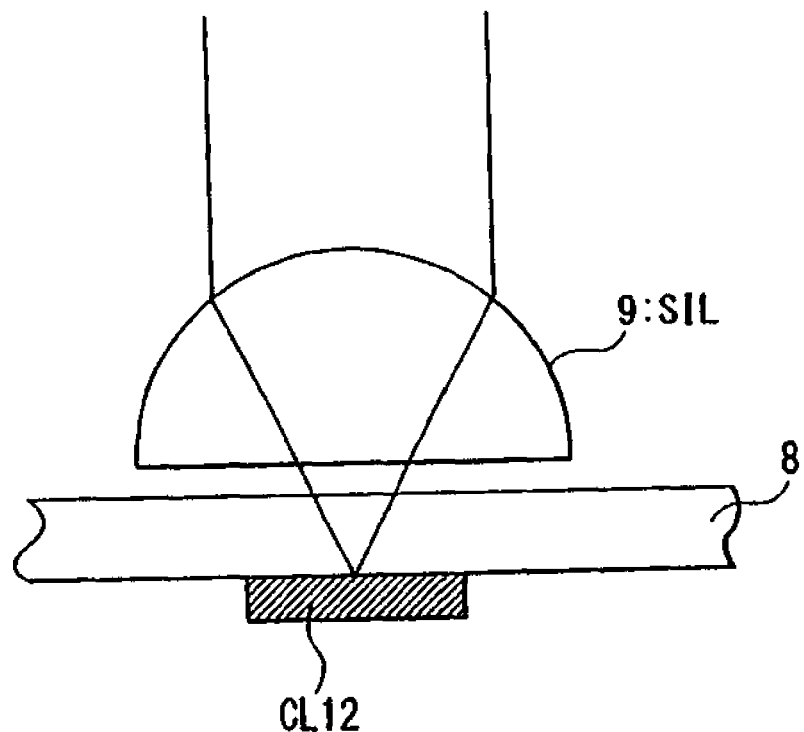
FIG. 18 is a partially enlarged view depicting a cell when a solid immersion lens is used.

FIG. 18 shows a partially enlarged view of cell CL12 of FIG. 16 wherein a solid immersion lens (called "SIL"), which has the same effect as an immersion lens, is used. In FIG. 18, components indicated by symbols 8 and CL12 are the same as those in FIG. 16, and number 9 indicates a solid immersion lens. Also, in this arrangement, the numerical aperture NA is improved by the solid immersion lens, thereby improving the S/N ratio still further.

If the substrate of the DNA chip 8 is required to be conductive, transparent electrodes made, for example, of an indium tin oxide (called "ITO") film may be placed on the transparent substrate. Hybridization can be accelerated by applying a positive voltage to the electrodes because the DNA is charged with negative electricity.

Figure 19:
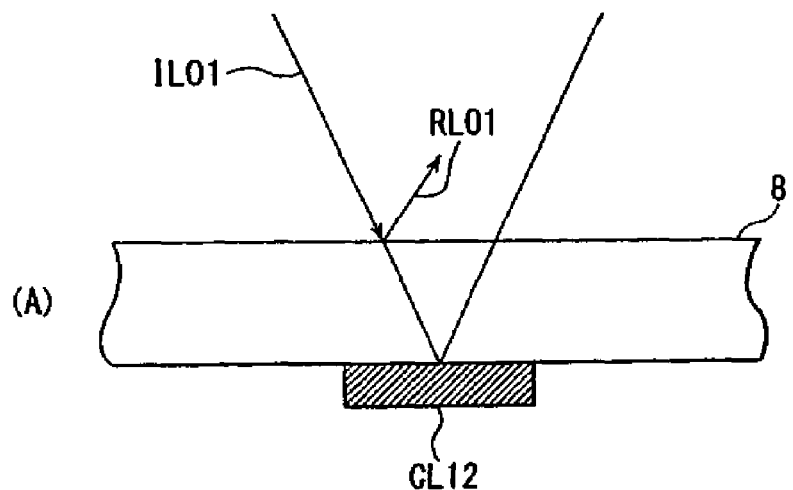
FIGS. 19(A) and 19(B) are schematic views depicting comparison between DNA chips with and without anti-reflection coating.
Figure 19:
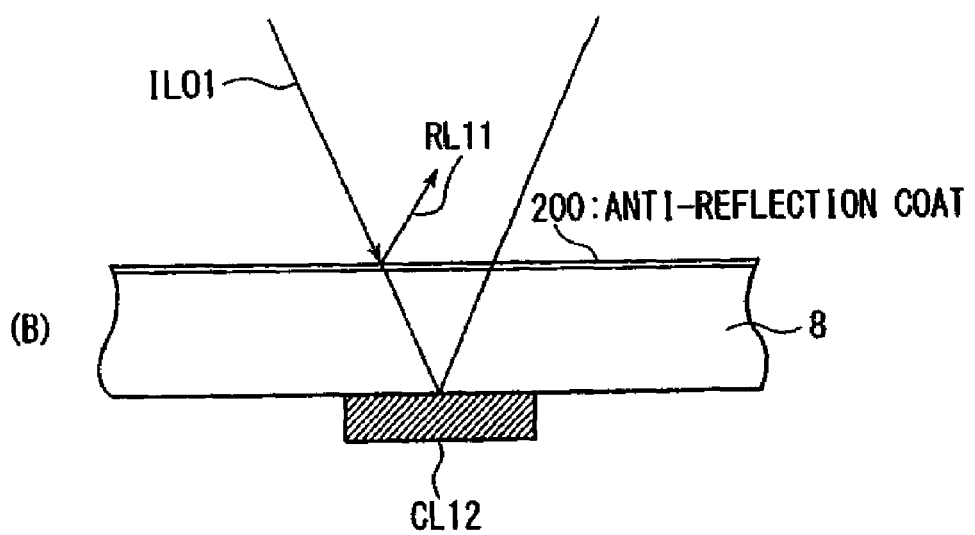

An anti-reflection coating, which may also comprise indium tin oxide, maybe placed on the surface of the DNA chip 8 opposite to that on which the cells are arranged. FIGS. 19(A) and (B) show a comparison between DNA chips with an anti-reflection coating, and without such coating, wherein in FIG. 19(A) components indicated by 8 and CL12 are the same as those in FIG. 16, and anti-reflection coating 200 is provided. The structure of the DNA chip 8 shown in FIG. 19(A) is the same as the one shown in FIG. 16. In FIG. 19(B) the anti-reflection coating 200 is formed on one side of the substrate of the DNA chip 8 opposite the side on which the cells, e.g. CL12, are arranged. In the case of FIG. 19(A), the ratio of reflected light RL01 to incident light IL01 is approximately 4%. In the case of FIG. 19(B), however, the ratio of reflected light RL11 to incident light IL11 is reduced to be as small as approximately 0.5%. Thus, the luminous energy of excitation light irradiated at cells CL12 on the DNA chip 8 is increased, which also improves the S/N ratio.

The side of the chip 8 on which the cells CL12 are arranged may be dry. Also, the same side may be wetted with hybridization liquid. Also, although a laser is shown, other types of excitation light sources may be used, such as an LED lamp, a zenon lamp, a halogen lamp, or other white light sources. Moreover, if a confocal optical system is used with the biochip reader, fluorescent light produced by dust particles, if any, can be removed more effectively. Hence, it is possible to further improve the S/N ratio, as compared with biochip readers using a non-confocal optical system.

To summarize, the invention attains the following and other advantages.

(1) The S/N ratio is improved by irradiating excitation light from one side of a transparent biochip opposite to that on which samples are arranged. Hence, cost is reduced.

(2) The numerical aperture NA can be improved by using an immersion lens or a solid immersion lens as the objective lens, whereby S/N ratio is further improved.

(3) The S/N ratio is still further improved, as compared with use of non-confocal optical systems, by using a confocal optical system as the biochip reader.

(4) The luminous energy of the excitation light irradiated at the samples increases because an anti-reflection coating formed on a side of the chip opposite the side on which the samples are arranged. This further increases the S/N ratio.

(5) Transparent electrodes may be formed on the transparent chip to accelerate hybridization by applying a positive voltage thereto since the DNA is charged with negative electricity.

(6) When samples used with the biochip reader are either DNA or RNA segments, known samples having a complementary sequence combine by hybridization with unknown samples marked with a fluorescent substance. Consequently, identification can be readily made of the sequence of the unknown samples.

(7) When samples used with the biochip reader are either protein segments or sugar chain segments, known samples combine by antigen antibody reaction with unknown samples. Thus, identification can be readily made of the sequence of the unknown samples.

In the embodiments of FIGS. 6-15, it is possible to use the types of samples discussed above, that is, DNA, RNA, protein and sugar chain. In, the embodiments of FIGS. 16-19, the optical detectors may be one of the means shown in FIGS. 6, 10, 12 and 13.

Figure 20:
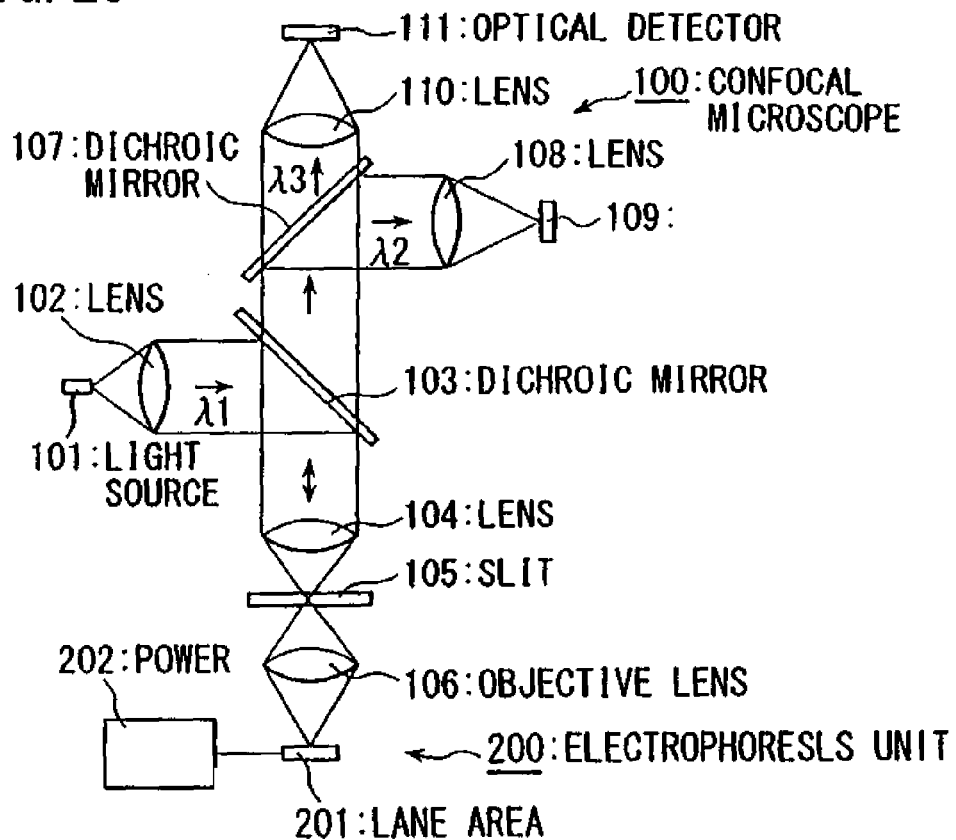
FIG. 20 is a block diagram depicting an illustrative polychrome electrophoresis system of the invention.

FIG. 20 shows a polychrome electrophoresis system comprising a confocal microscope 100 and an electrophoresis unit 200. The confocal microscope 100 (also referred to as "confocal optical scanner") is designed to be able to optically scan the gel in a lane 201 and read the electrophoresis pattern of fluorescent light emitted from the gel. Excitation light, e.g. blue laser light with a wavelength of λ1, emitted by a light source 101 is made parallel by a lens 102, is then reflected by a dichroic mirror 103, and then is condensed onto the slits of slit array 105 through a lens 104. Excitation light that has passed through the slits 105 is narrowed by an objective lens 106 and enters the gel in the lane area 201. The fluorescent substance in the lane area 201 is excited by this light and emits fluorescent light.

Figure 21:
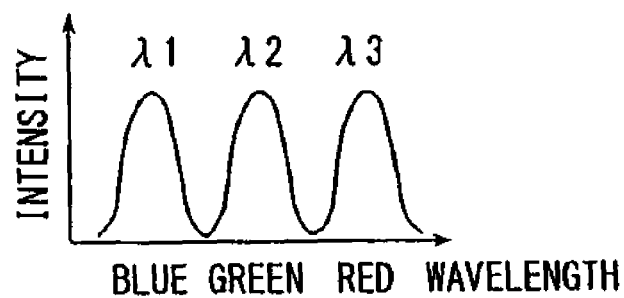
FIG. 21 is a graph depicting distribution of wavelengths of excitation light and fluorescent light.

The fluorescent light thus produce is then transmitted to follow the same path that the excitation light followed, by passing through objective lens 106, slit array 105, lens 104, dichroic mirror 103, to reach another dichroic mirror 107, then through lens 110 to detector 111, and through lens 108 to detector 109. It should be noted that the dichroic mirror 103 reflects light with a wavelength of λ1, e.g. blue, and allows light with wavelengths greater than λ1 to pass therethrough. Likewise, dichroic mirror 107 reflects light with a wavelength of λ2, e.g. green, and allows light with a wavelength λ3, e.g. red, to pass therethrough. The relationship among the wavelengths λ1, λ2, and λ3 is as shown in FIG. 21.

Light having a wavelength of 2 that is reflected by dichroic mirror 107 is condensed onto optical detector 109 through lens 108. On the other hand, light having a wavelength of 3 is passed through dichroic mirror 107 and is condensed onto an optical detector 111 through lens 110, as depicted.

When slit array 105 is moved and controlled in such a manner that light emitted by light source 101 scans across the surface of lane area 201, the electrophoresis pattern of fluorescence produced in the lane area 201 is formed at each of the optical detectors 109 and 111. At this point, only the electrophoresis pattern of green fluorescence is formed at optical detector 109, whereas only the electrophoresis pattern of red fluorescence is formed at detector 111. The optical detectors 109 and 111 convert the images to electrical signals and provide output signals thereof.

The electrophoresis unit 200 is equipped with the lane area 201 and power unit 202 for supplying voltage to cause electrophoresis in the lane area 201.

As described, using a confocal optical scanner enables easy and precise measurement of polychrome electrophoresis patterns of fluorescence produced in lane area 201.

Figure 22:
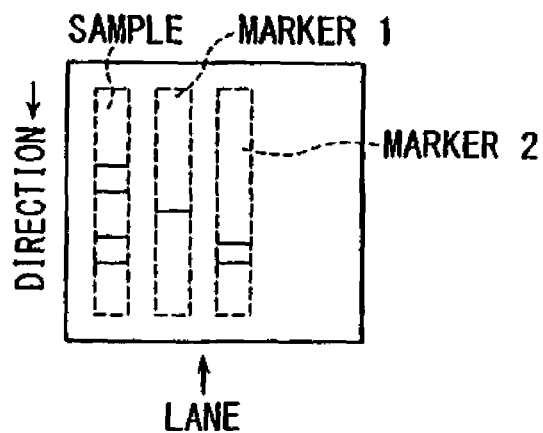
FIG. 22 is a schematic view depicting arrangement of samples and markers.

Normally, however, it is not possible to determine the absolute value of molecular weight by electrophoresis. Thus, under normal conditions, reference marker molecules are supplied into neighboring lanes, as shown in FIG. 22. This method is, however, problematical since it requires more space and involves measurement errors due to difficulty in applying voltage evenly to all of the lanes.

Figure 23:
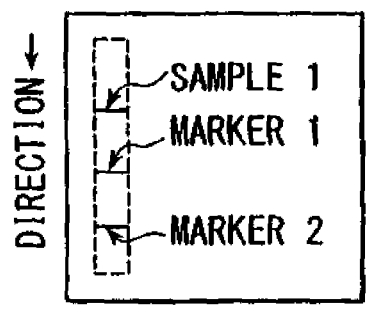
FIG. 23 is a schematic view depicting an arrangement where samples and markers are injected into the same lane.

In the invention, advantageously, a sample is supplied together with a reference marker molecule (called "marker") into the same lane, as shown in FIG. 23. At this point, coloring matters having different wavelengths of fluorescence are combined with the respective markers and samples. A material thus prepared is submitted to electrophoresis and scanned with the confocal optical scanner. Thus, it is possible with the invention to detect two or more electrophoresis patterns of fluorescence at the same time.

Figure 24:
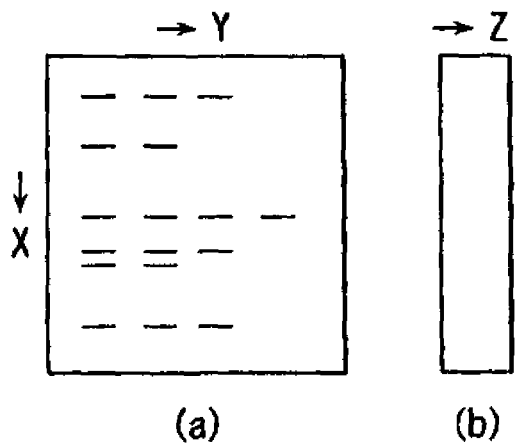
FIG. 24 is a schematic view depicting a lane area when three-dimensional electrophoresis is conducted.

FIG. 24 shows another example of electrophoresis by the embodiment of FIG. 20. Unlike prior known two-dimensional electrophoresis the FIG. 24 embodiment provides three dimensional electrophoresis wherein another dimension is added in the depth direction (Z-axis direction). In this example, method for applying a voltage gradient and a pH gradient in the X-axis (longitudinal), Y-axis (lateral) and Z-axis (depth) directions include:

(1) applying high voltage in the x-axis direction, pH gradient in the Y-axis direction and low voltage in the Z-axis direction.

(2) applying voltage in the x-axis direction, pH gradient in the Y-axis direction and multi-layer gel with each layer having a different concentration in the Z-axis direction.

(3) applying voltage in the X-axis direction, pH gradient in the Y-axis direction and a voltage gradient in the Z-axis direction, in order to perform affinity electrophoresis.

In this embodiment, the electrophoresis system optically scans the surface of the lane area 201 by being moved up and down along the optical axis (e.g. in the Z-axis direction). For example, the objective lens 106 of the confocal optical scanner 100 can be moved up and down. Then, X-Y axis polychrome electrophoresis patterns of fluorescence are detected by controlling the optically scanned surface in the Z-axis direction. Consequently, it is possible with the invention to easily acquire three dimensional information.

In the above discussion, only specific preferred embodiments are provided for purposes of describing the invention and showing examples of carrying out the invention. The embodiments are therefore to be considered as illustrative and not restrictive. The invention may be embodied in other ways without departing from the spirit and essential characteristics thereof. Accordingly, it should be understood that all modifications and extensions thereof are to be considered to be within the spirit and scope of the invention.

Figure 25:
FIG. 25 is a schematic view depicting where a lane on each axis is isolated.

For example, the X-Z plane shown in FIG. 25 may be used as the lane in the embodiment of FIG. 24 to reduce the lane area, compared with that for two dimensional electrophoresis. In addition, the distribution of concentration in the depth direction (Z-axis) can be realized by wetting one side of the substrate with a highly concentrated solution by applying a density gradient in the depth direction by means of centrifugation. This distribution can also be realized by stacking multiple layers of gel with different concentrations.

Figure 26:
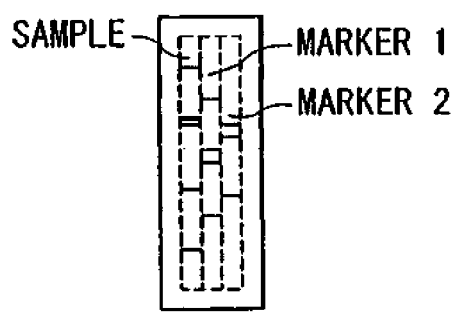
FIG. 26 is a schematic view depicting where markers are arranged along the depth of the samples.

If samples and markers are placed separately in the depth direction, as shown in FIG. 26, it is possible to perform measurement using a compact electrophoresis system with all other conditions being the same as those in FIG. 25. In this case, the same fluorescence color may be used since lanes can be isolated in the depth direction by a confocal method.

Figure 27:
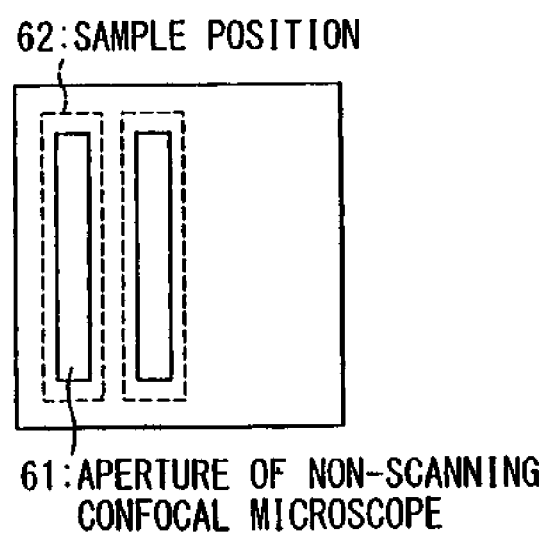
FIG. 27 is a schematic view depicting the relationship between sample positions and apertures.

When analyzing electrophoresis using a non-scanning confocal microscope, a sample may be positioned so that the aperture 61 of the confocal microscope is aligned with the sample position 62 or with part of the sample, as shown in FIG. 27. Hence, it is possible to perform measurement with the invention with higher S/N ratios and without adverse effect that may result when the edges of the sample are measured.

The light source may comprise a single grating or two photon excitation light because these sources have the same effect.

The following and other advantages are attained by the invention.

(1) A highly precise polychrome electrophoresis is realized using a compact system.

(2) A three dimensional electrophoresis is realized using a compact system, and wherein a large amount of interrelated information can thus be acquired in a shorter length of time.

Also, the three dimensional electrophoresis system comprises:

(1) an electrophoresis unit wherein various types of target substance, such as protein or DNA, are supplied into a lane area and gradients of various physical quantities, such as voltage, pH, density and concentration, are used for electrophoresis; and (2) a scanning or non-scanning confocal microscope or 2 photon excitation microscope, wherein a sample in the lane area is scanned with excitation light and the fluorescence pattern of the sample produced by the excitation light is detected, thereby to detect the three dimensional position and concentration of the sample.

In the electrophoresis system, any of the microscopes shown in FIGS. 6-15 may be used in place of a scanning or non-scanning confocal microscope of 2 photo excitation microscope.

What is claimed is:

1. A combination, comprising:
a biochip on which a plurality of samples are provided as spots or an array in a two dimensional manner on a surface of said biochip, and
a biochip reader comprising:
a microscopic optical system selected from the group consisting of a scanning confocal optical system, a non-scanning confocal optical system, and a 2-photon excitation optical system;
a light source which irradiates excitation light simultaneously on a plurality of samples provided as spots or an array in a two dimensional manner on a surface of a biochip, and which causes said plurality of samples to emit fluorescent light different in wavelength from said excitation light;
a single optical detector which detects said fluorescent light emitted by said plurality of samples as spectroscopic information; and
a grating, a prism spectrometer, dichroic mirrors, or a Fourier spectrometer which refracts said fluorescent light emitted by said samples and develops said fluorescent light as said spectroscopic information at different locations on said single optical detector according to wavelength, said spectroscopic information being developed between images of adjacent samples among said plurality of samples, wherein said spectroscopic information is detected by said single optical detector in a two dimensional manner.

2. The combination of claim 1, wherein said biochip reader further comprises a shield having a plurality of apertures aligned with positions of each of said plurality of samples, said shield being disposed between said light source and said biochip, and wherein the area of spectroscopy is restricted by said apertures.

3. The combination of claim 2, wherein said excitation light from said light source is irradiated onto one side of said biochip which is opposite to a side surface where said plurality of samples are arranged.

* * * * *